US00PP20327P3

(12) United States Plant Patent

Janse van Rensburg

(10) Patent No.: US PP20,327 P3

(45) Date of Patent: Sep. 22, 2009

(54) MANDARIN NAMED 'AFRICAN SUNSET'

(50) Latin Name: *Citrus L.*
Varietal Denomination: African Sunset

(75) Inventor: George Diederick Janse van Rensburg, Nelspruit (ZA)

(73) Assignee: Agricultural Research Council, Hatfield (ZA)

( * ) Notice: Subject to any disclaimer, the term of this patent is extended or adjusted under 35 U.S.C. 154(b) by 0 days.

(21) Appl. No.: 11/986,349

(22) Filed: Nov. 20, 2007

(65) Prior Publication Data

US 2009/0138999 P1 May 28, 2009

(51) Int. Cl.
*A01H 5/00* (2006.01)

(52) U.S. Cl. ..... Plt./202

(58) Field of Classification Search ..... Plt./202
See application file for complete search history.

(56) References Cited

PUBLICATIONS

UPOV–ROM GTITM Plant Variety Database Jan. 2008, GTI Jouve Retrieval Software citation for 'African Sunset'.*

"Certificate of grant of a Plant Breeder's Right," issued Nov. 7, 2004 in respect of plant *Citrus* L. (Mandarin), of variety African Sunset. Department of Agriculture, Republic of South Africa. (1 page).

* cited by examiner

*Primary Examiner*—Annette H Para
(74) *Attorney, Agent, or Firm*—Morrison & Foerster LLP

(57) ABSTRACT

A new variety of mandarin (*Citrus* L.) designated 'African Sunset' is described. The fruit matures earlier than comparable varieties. In addition, the fruit includes a more pebbled rind, a lower acid content, and is almost seedless.

6 Drawing Sheets

Botanical/commercial classification: (*Citrus* L.), new mandarin variety.

Variety denomination: 'African Sunset'.

BACKGROUND OF THE INVENTION

African Sunset is a hybrid of an unpatented *Citrus reticulata* variety Ellendale (the pollen parent) and an unpatented mandarin hybrid variety Robin (the seed parent). In 1980, pollen from 'Robin' (unpatented) was applied by hand to the stigmas of 'Ellendale' (unpatented). The resulting fruits were collected in June 1981 where after seeds from each fruit were extracted and irradiated and thereafter planted in 1982. The resulting 73 seedlings were transplanted to a breeding orchard situated at Addo, in the Eastern Cape province of the Republic of South Africa (global positioning satellite co-ordinates 25°42'E; 33°34'S). These seedlings were not grafted and were grown on their own roots. Due to the so-called juvenility phenomenon in citrus trees as is known in the art, trees resulting from these transplanted seedlings only bore fruit in 1992. These trees were then evaluated for fruit quality traits. Based on the results of this evaluation, six of the aforementioned trees were selected for further evaluation, of which one of these selections resulted in the present 'African Sunset' variety. Thereafter 'African Sunset' was made subject of a South African Plant Breeders' Rights application in January 2000. This application was granted in 2004 under number ZA 20043212.

Some fruit splitting of the variety does occur in March/April. Trees are alternate-bearing and fruit size may be unacceptably large without manipulation. Additionally, fruit from young trees (3 to 4 years) are normally coarse and prone to granulation.

'African Sunset' was first asexually propagated in Addo, South Africa in 1995 when buds were collected from a hybrid seedling designated X83-2505/3, and then budded onto 'Carizzo citrange' rootstocks. Ten trees of 'African Sunset' were planted in the field in September 1996 for description purposes. All characteristics of the original tree and its fruit as determined and described appear to be transmitted through succeeding asexual propagations. While 'African Sunset' has been propagated and grown on 'Carizzo citrange' rootstock, no incompatibility or other rootstock related problems have been observed. The mother tree is growing on its own roots and is currently (2008) 24 years old. Although the tree condition is beginning to decline, the fruit quality is and always has been good.

'African Sunset' has been cleansed of all viruses and viroids by shoot-tip grafting (STG), followed by immunisation with *Citrus tristeza* virus LMS6. This was done through a regulated process, which involves taking vegetative buds from the mother tree and introducing same into the South African Citrus Improvement Scheme. In this process, plant material is shoot-tip grafted to provide a virus-free source of bud wood material. Material so obtained is then pre-immunized with a mild strain of the aforementioned *Citrus tristeza* virus, followed by a certification by the Citrus Foundation Block.

The applicant is aware of U.S. Plant Pat. No. 16,289 ('289). The present variety is distinguishable over '289 in that, inter alia, not only is the present variety diploid whereas '289 is triploid, but also the respective rind colors differ.

BRIEF SUMMARY OF THE INVENTION

In this specification, all major color code designations are made with reference to the R.H.S. Color Chart (1986) as provided by the Royal Horticultural Society of Great Britain.

This invention relates to a new and distinct variety of mandarin (*Citrus reticulata*), presently named 'African Sunset', the novel characteristics of which, under the local evaluation conditions, reside particularly in the early onset of maturity of the fruit (mid-late June) as opposed to July/August when compared to 'Ellendale' (unpatented). In addition to the above, a further novel and distinctive feature of 'African Sunset', as compared to 'Ellendale' (unpatented), include a more pebbled rind and a lower acid content, and is almost seedless, even in mixed blocks.

BRIEF DESCRIPTION OF THE DRAWINGS

FIG. 2(*b*): is a photograph showing a second perspective of the stem;

DETAILED BOTANICAL DESCRIPTION

Figure 1:
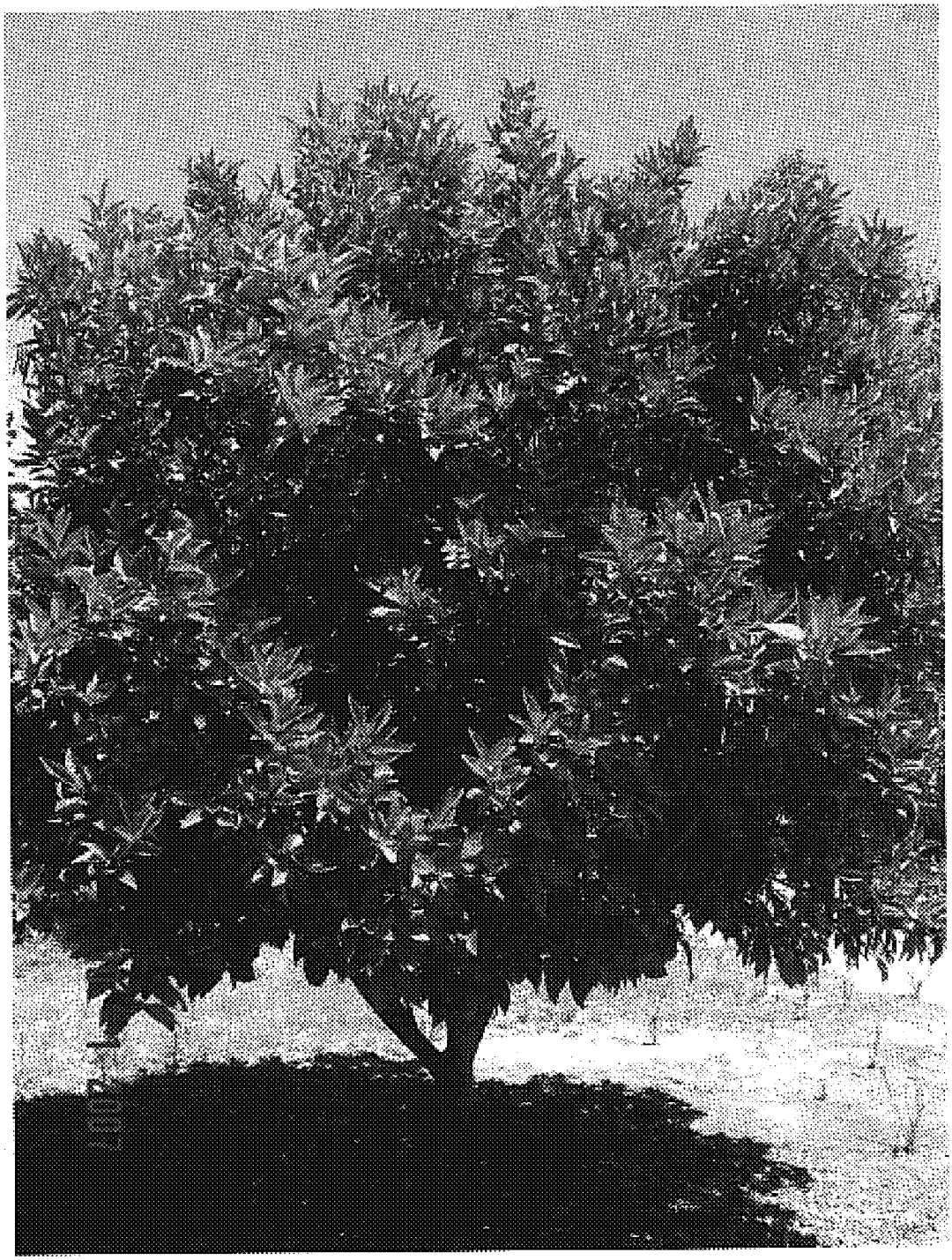
FIG. 1: is a photograph showing an entire tree.
Figure 2A:
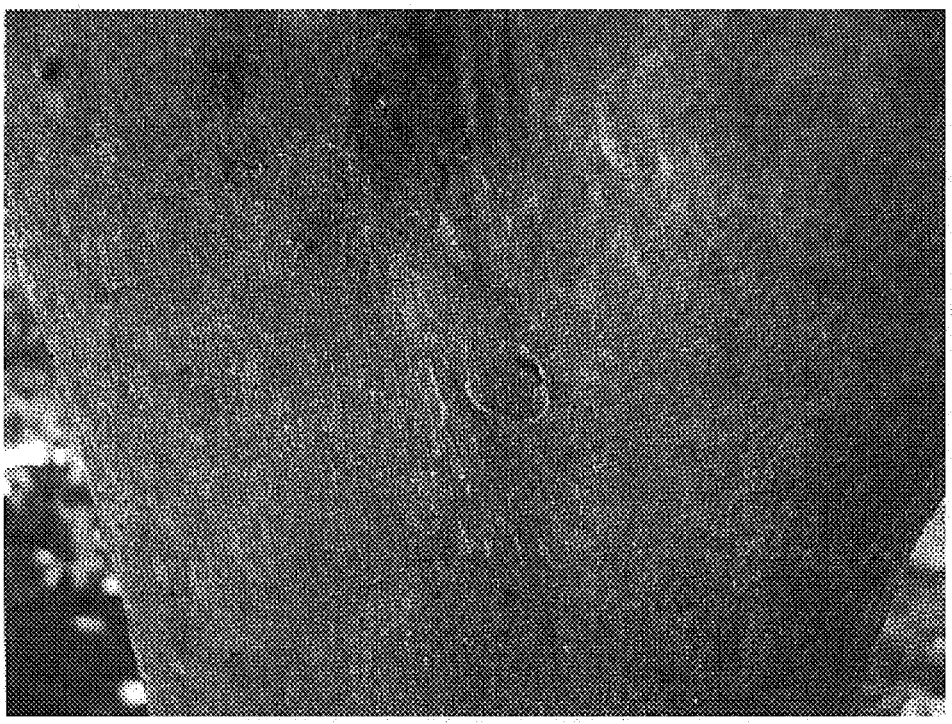
FIG. 2(*a*): is a photograph showing a first perspective of the stem.
Figure 2B:
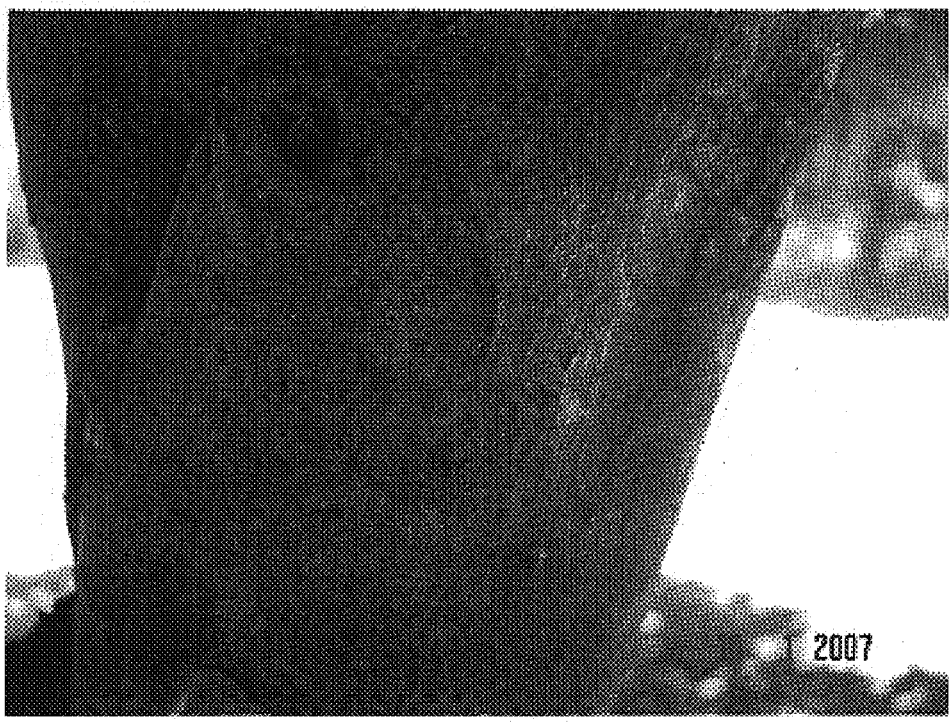
Figure 3:
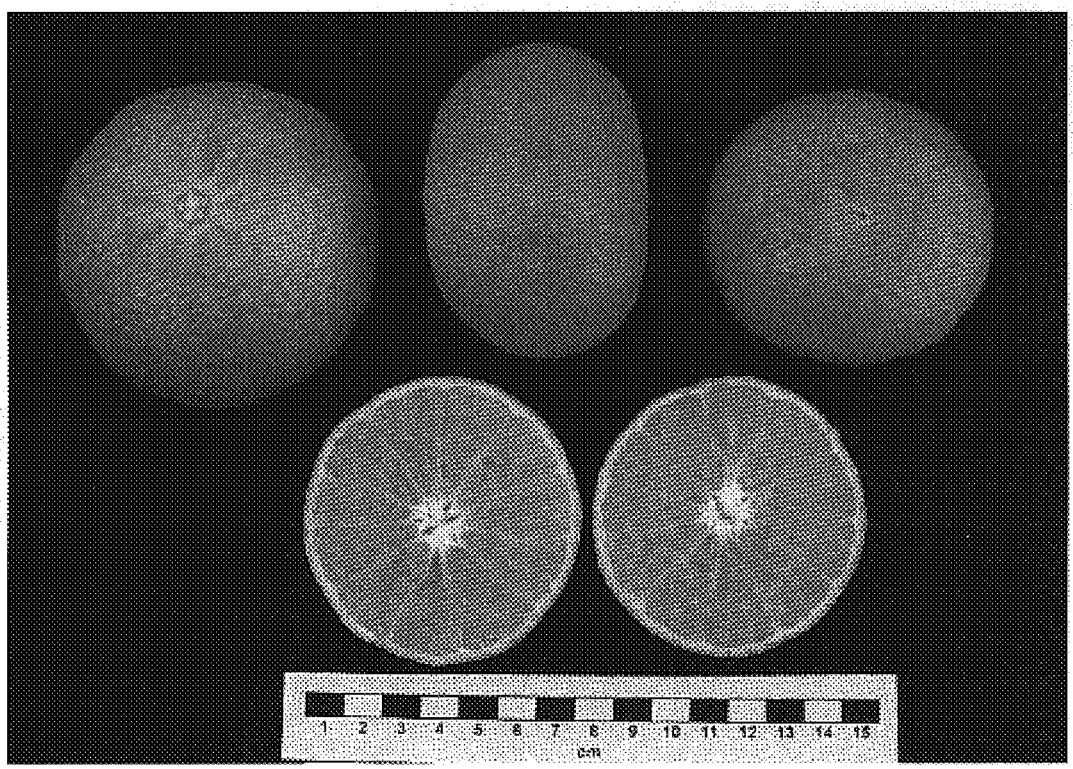
FIG. 3: is a photograph showing details of the fruit: viewed from the side, apex, base and including a cross section through the fruit, illustrating the obloid shape of the fruit as well as its size and color of the rind.
Figure 4:
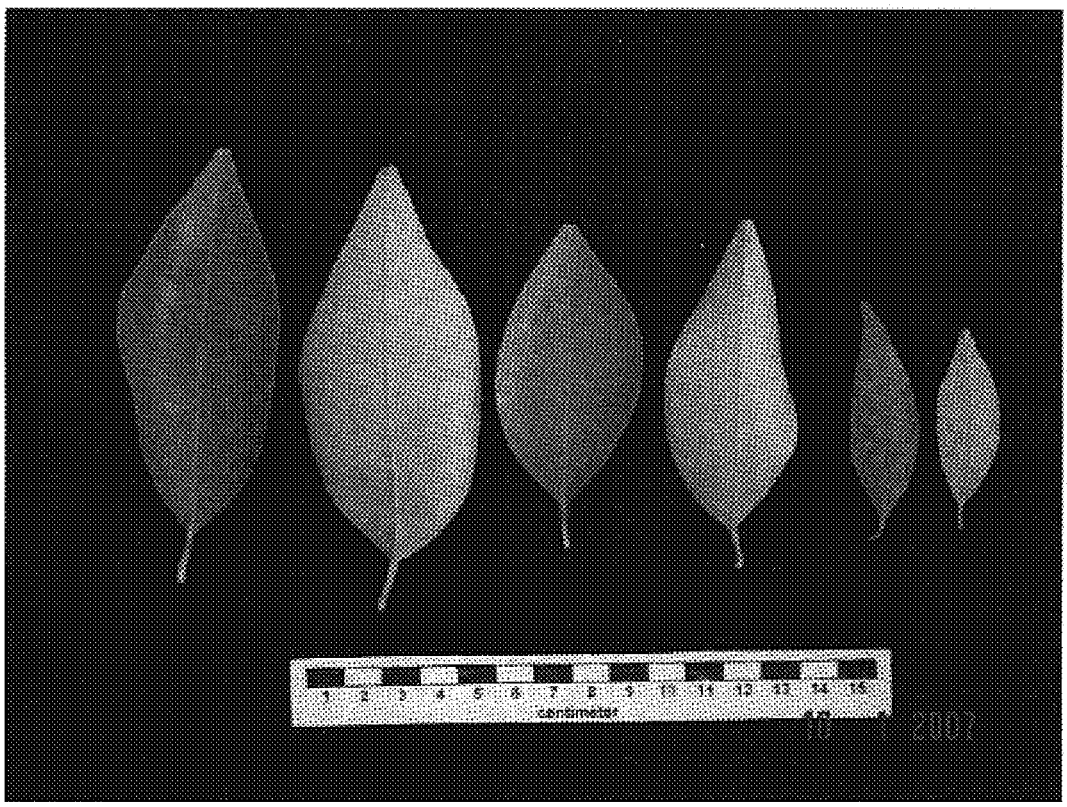
FIG. 4: is a close-up photograph showing several leaves of 'African Sunset', illustrating the sizes and shapes of the leaves, including the venation thereof.
Figure 5:
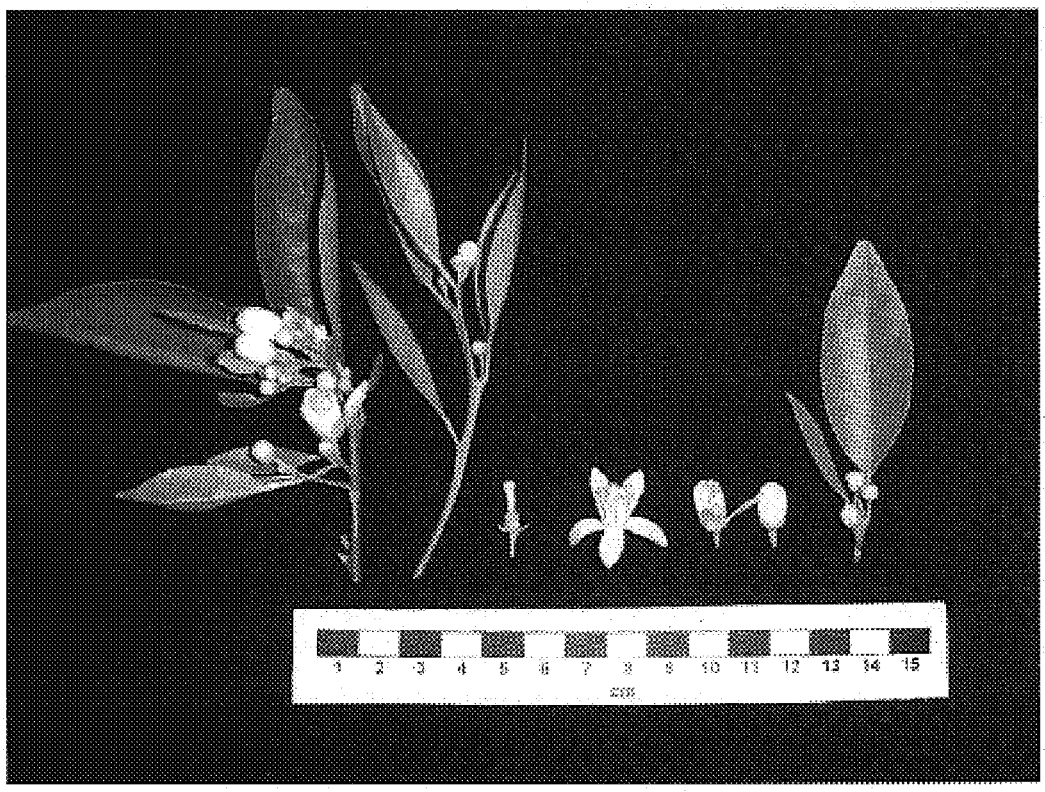
FIG. 5: is a photograph showing inflorescence.
Figure 6:
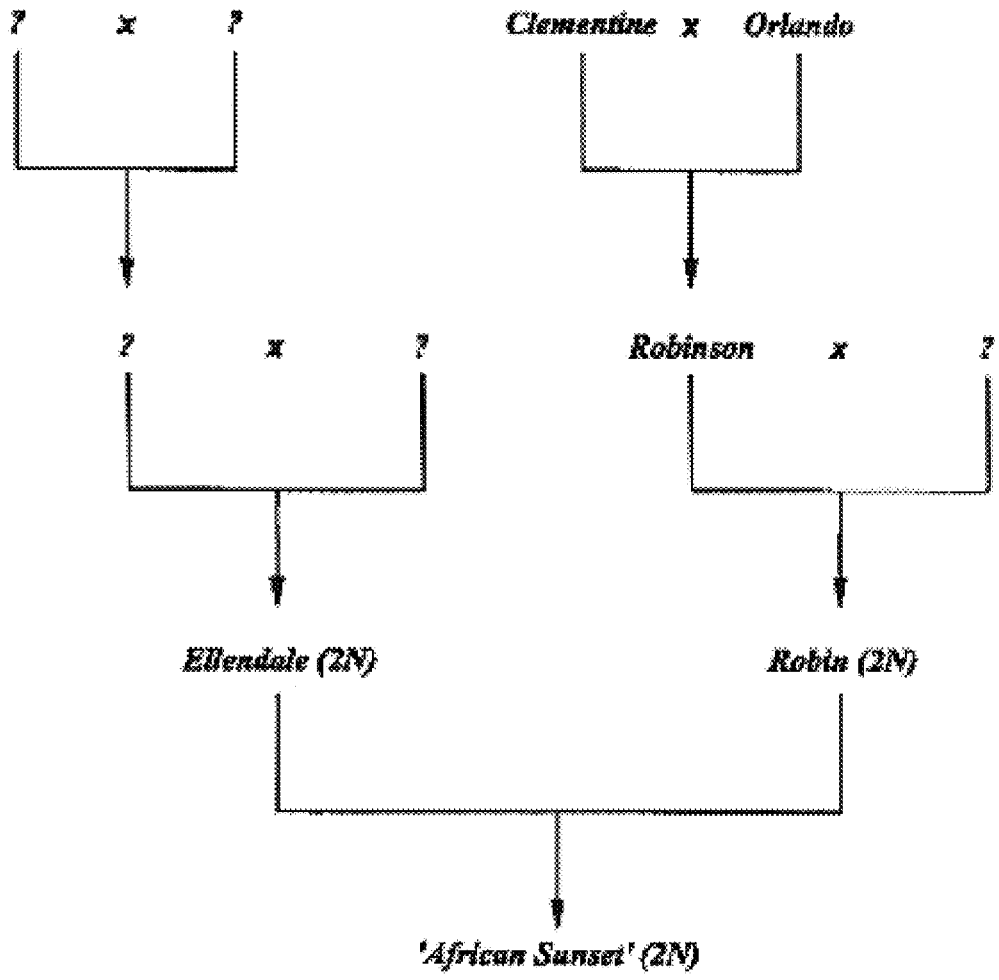
FIG. 6: is a schematic illustration of the pedigree of 'African Sunset'.

The below detailed botanical description of 'African Sunset' is based on 4 to 6, and 11 year old trees, unless otherwise specifically stated to the contrary.

Tree: 'African Sunset' trees are moderately spreading and thornless. Tree vigor and density is medium. Rootstock compatibility with 'Carizzo citrange' is median as observed and indicated by stem measurements. Trunk color is greyish-brown (RHS 197A) and the trunk has a smooth surface texture.

*Shape.*—Spheroid in shape.

*Size.*—In eleven year-old trees, the average tree height is 3.0 meters, while the average width is 2.94 meters. Average trunk circumference of an eleven-year old tree is 454 millimeters at the bud union, and an average of 399 millimeters and 475 millimeters at heights of 150 millimeters above and below the bud union, respectively. The average height of the bud union is 200 millimeters above soil level. Branches are on average 120 millimeters in circumference. There are on average 3 main branches per tree, with an average crotch angle of 75°. Branch texture is smooth and has a greyish-brown color (RHS 197A).

Flower: 'African Sunset' trees flower from September to October in South Africa. Being a normal diploid mandarin, 'African Sunset' produces abundant pollen and has, depending on the climate, 30.9% pollen viability (determined using the carmine-red stain method).

*Size.*—The flower of 'African Sunset' is typically hermaphroditic. Flower buds are obovoid in shape and have an average calyx diameter of 5.6 millimeters and is an average 10 millimeters in length. Each flower has between 4 and 5 petals. Petals are elliptic in shape and each have a length of 11.4 millimeters and a width of 5.0 millimeters. The petal tip is acute in shape, while the base is truncate. The petal margin is entire. There are also 3 observed flowers per cluster and flowers have a typical citrus flower fragrance.

*Color.*—The petals are yellow-white (RHS 158B) on the inside and yellow-white (RHS 158B) with small, yellow speckles (RHS 8C) on the outside. Further, light yellow (RHS 8C) anthers are present.

*Reproductive organs.*—The stigma with style is an average 6.4 millimeters in length, while the stamen is 7.8 millimeters in length. One style and one stigma are present with an average of 16.8 stamens.

Young shoot. —Anthocyanin coloration of the tip is absent.

Leaves: Leaf descriptions hereunder were taken as the first leaf after new flush growth.

*Shape and size.*—Leaves are simple, sessile, broad and are elliptically-shaped with entire blade margins. The leaves also have typically pinnate venation and the leaf apex is acuminate in shape, while the base is rounded. Blade length is 85 millimeters, while blade width is 38 millimeters. Accordingly, blade length to width ratio is 2.24:1. Emargination of the blade is present at the tip, however, incisions of the blade margin is absent. In cross-section, the shape of the leaf is slightly concave and generally flattened. It also warrants mentioning that 'African Sunset' leaves are totally without thorns. In fact, even young trees in the nursery do not have thorns.

*Color.*—Generally, the upper (adaxial) leaf surface is darker then the lower (abaxial) leaf surface. Adaxial color is green (RHS 137A), while abaxial color is yellow-green (RHS 146B). Furthermore, leaves have a smooth adaxial surface, while the abaxial surface has prominent veins.

*Petiole.*—Petiole length is 10.5 millimeters and there are no wings on the petioles.

Fruit, external characteristics:

*Color.*—The external fruit color is orange-red (a combination of RHS 28A, 30B and 25A). Fruit are sensitive to wind scarring.

*Surface.*—Pubescence is absent on the fruit surface. Oil glands are uniform in size and pitting and pebbling are present with pitting medium to dense and a medium to strong degree of dense pebbling.

*Shape.*—With reference to the Citrus descriptors of the previously named International Plant Genetic Resources Institute (IPGRI), now known as Biodiversity International, the shape of 'African Sunset' is obloid, having its broadest part in the middle of the fruit. The fruit length to diameter ratio is 0.714. The general shape of the proximal part of the fruit is flattened. In comparison, fruit obtained from 'Nour' (unpatented) is generally flatter and larger than fruit obtained from 'African Sunset'.

*Size.*—Fruit is on average 50 millimeters in length and 70 millimeters in diameter, with an average mass of 155.7 grams (see Table 1 below) when grown on 'Carrizo citrange' rootstock.

*Base.*—The general shape of the distal part of the fruit is flattened, and depression is shallow to absent. Radial grooves are absent.

*Stalk end.*—Shallow depression evident with many radial grooves.

*Areola.*—Has complete areola, which is smooth and complete in appearance, having an average diameter of 2.1 millimeters.

*Stylar scar.*—Present, but small in size.

Fruit, internal characteristics:

*Color.*—Flesh color is dark orange (RHS 28A).

*Navel.*—Occasionally present when viewed internally.

*Oil glands.*—Oil glands on the inner rind absent.

*Glandular layer.*—Rag is moderately tough.

*Mesocarp* (*albedo*).—The fruit peels moderately easily and has a rind on average 3 millimeters thick. The adherence of albedo to pulp is medium and very few to no albedo strands are left behind after peeling. Albedo color is yellow-range (RHS 23D and 19C).

*Axis.*—Fruit has an open core with a diameter of 14 millimeters. There appears to be a sparse to no filling in the core.

*Segments.*—The number of well-developed segments is on average 10.5 per fruit.

*Pulp.*—Coarser texture with smaller cells. Juice vesicles are short to medium in size. In transverse section, the fruit pulp is scalloped in shape.

*Juice.*—Fruit have a rich 'Navel'-like flavor and although the rag is tougher than that of 'Clementine' (unpatented), it is still within acceptable standards. Fruit has an average juice percentage of 59.7% and 58.6%, when grown on its own roots and on 'Carrizo citrange' rootstock, respectively. Solids: acids ratio indicated that the best time to harvest fruit at Addo, South Africa, is mid-end June.

*Seeds.*—Seed are ovoid to semi-deltoid in shape with a slightly wrinkled almost smooth surface, a length of 1.2 mm and a width of 0.8 mm and is fairly flat. Seed number is not excessive in mixed blocks and fruit are commercially seedless (no fruit has greater than 3 seeds) when caged. In a highly cross-pollinated scenario 86.9% (Table 1) of the fruit had no seeds and 13.1% had between 1–3 seeds per fruit. Therefore, this selection should be almost seedless in a solid block although it is probably not self-incompatible.

Table 1: 'African Sunset' Selections: Average of Internal Quality Tests 2001 to 2006—Addo, South Africa

TABLE 1

'African Sunset' Selections:
Average of Internal Quality Tests 2001 to 2006-Addo, South Africa

| Cultivar | Rootstock | Juice % | Brix % | Acid % | Brix:Acid Ratio |
|---|---|---|---|---|---|
| 'African Sunset' | 'Carrizo' | 58.6 | 13.1 | 2.4 | 11.5 |
| 'African Sunset' | Own roots | 59.7 | 13.0 | 0.8 | 15.7 |

TABLE 1-continued

'African Sunset' Selections:
Average of Internal Quality Tests 2001 to 2006-Addo, South Africa

| Cultivar | Percentage fruit with 0 seed per fruit | 1-3 | 4-6 | 7+ | Avg. Fruit Mass (grams) |
|---|---|---|---|---|---|
| 'African Sunset' | 92.2 | 7.8 | 0.0 | 0.0 | 155.1 |
| 'African Sunset' | 86.9 | 13.1 | 0.0 | 0.0 | 156.3 |

Table 2: Internal Quality Tests (trees planted in 1984):

TABLE 2

Internal Quality Tests (trees planted in 1984):

| Test Date | Juice % | Brix % | T. Acid % | Brix/TA Ratio |
|---|---|---|---|---|
| 28 Jun. 1994 | 54 | 11.0 | 0.90 | 12.1 |
| 11 Jul. 1997 | 56 | 12.0 | 0.82 | 14.6 |
| 25 Jul. 2002 | 63 | 14.4 | 1.08 | 13.3 |
| 14 Jul. 2004 | 58 | 12.4 | 0.85 | 14.6 |

Table 3: African Sunset yields 2001 to 2006 at Addo, South Africa.

TABLE 3

African Sunset yields 2001 to 2006 at Addo, South Africa.

| | Year 2001 | 2002 | 2003 | 2004 | 2005 | 2006 | 2007 |
|---|---|---|---|---|---|---|---|
| Treeage (Yrs) | 4 | 5 | 6 | 7 | 8 | 9 | 10 |
| Ton/ha | 10 | 21 | 35 | 38 | 24 | 42 | 50 |
| Kg/tree | 11 | 23 | 38 | 42 | 26 | 46 | 55 |

The fruit of 'African Sunset' is intended for consumption. Fruit stored and shipped at 4° C. and kept under these conditions, are likely to keep for up to 6 weeks.

The above described new variety of Mandarin displays an early onset of maturity of the fruit (mid-late June) and a more pebbled rind and a lower acid content as compared to known varieties.

What we claim is:

1. A novel and distinct variety of mandarin tree having the characteristics described and illustrated herein.

* * * * *